United States Patent [19]

Tano et al.

[11] Patent Number: 4,528,403
[45] Date of Patent: Jul. 9, 1985

[54] HYDROFORMYLATION PROCESS FOR PREPARATION OF ALDEHYDES AND ALCOHOLS

[75] Inventors: Kazuo Tano, Yokohama; Keiichi Sato, Kawasaki; Toru Okoshi, Yokohama, all of Japan

[73] Assignee: Mitsubishi Chemical Industries Ltd., Tokyo, Japan

[21] Appl. No.: 535,783

[22] Filed: Sep. 26, 1983

[30] Foreign Application Priority Data

Oct. 21, 1982 [JP] Japan ................................. 57-184858
Nov. 24, 1982 [JP] Japan ................................. 57-205623

[51] Int. Cl.$^3$ ............................................. C07C 45/50
[52] U.S. Cl. ....................................... 568/454; 568/909
[58] Field of Search ................. 568/909, 882, 454, 883

[56] References Cited

U.S. PATENT DOCUMENTS

| | | | |
|---|---|---|---|
| 3,954,877 | 5/1976 | Gipson | 568/454 |
| 4,221,743 | 9/1980 | Halstead | 568/454 |
| 4,260,828 | 4/1981 | Morrell et al. | 568/454 |
| 4,400,547 | 8/1982 | Dawes et al. | 568/454 |
| 4,420,640 | 12/1983 | Matsumoto et al. | 568/454 |
| 4,443,638 | 4/1984 | Yates | 568/454 |

OTHER PUBLICATIONS

Journal of Organometallic Chemistry, 52 (1975) pp. C55–C57, "Preliminary Communication".

*Primary Examiner*—Werren B. Lone
*Attorney, Agent, or Firm*—Oblon, Fisher, Spivak, McClelland & Maier

[57] ABSTRACT

A hydroformylation process which comprises hydroformylating an olefinic compound by reacting it with water gas in a catalyst solution containing rhodium and an oxide of an organic trivalent phosphorus compound; adding an organic trivalent phosphorus compound to the reaction mixture, followed by distillation to separate a distillate containing the hydroformylation product from a high-boiling residue containing rhodium; oxidizing the high-boiling residue at the same time as or subsequent to the distillation, to convert the organic trivalent phosphorus compound to its oxide; and recycling the oxidized residue to the hydroformylation reaction zone.

15 Claims, No Drawings

HYDROFORMYLATION PROCESS FOR PREPARATION OF ALDEHYDES AND ALCOHOLS

The present invention relates to a hydroformylation process. More particularly, the present invention relates to a process for hydroformylating an olefinic compound wherein a rhodium catalyst modified with an organic phosphorus compound is recycled in a catalytically active state for the hydroformylation reaction.

A process for producing an aldehyde or an alcohol as its hydrogenation product by reacting an olefinic compound with water gas in the presence of a catalyst, is well known as a so-called hydroformylation process. As the catalyst, a carbonyl complex of cobalt or rhodium is commonly used. It is known that when a rhodium carbonyl is employed, a particularly high catalytic activity and high selectivity for the aldehyde are obtainable. However, the rhodium carbonyl is unstable, and therefore it is common to use a rhodium carbonyl modified with a ligand containing e.g. phosphorus, arsenic or antimony. As such a ligand, an organic phosphine such as triphenylphosphine is preferably used. However, it is also known that an oxide of an organic trivalent phosphorus compound is useful. Particularly when used for the hydroformylation of a branched olefinic compound, a rhodium catalyst modified with an oxide of an organic trivalent phosphorus compound exhibits a high catalytic activity. However, the rhodium catalyst modified with the oxide of an organic trivalent phosphorus compound is relatively unstable. Accordingly, when the reaction mixture containing this catalyst is subjected to distillation to distill the formed aldehyde or alcohol, the catalyst undergoes decomposition, whereby rhodium will be precipitated. Thus, in the hydroformylation reaction wherein a rhodium catalyst modified with an oxide of an organic trivalent phosphorus compound is used, it used to be required firstly to decompose the rhodium catalyst in the reaction mixture and separate rhodium in the form of metal or an insoluble compound and then to subject the reaction mixture to distillation for the recovery of the product.

As opposed to such a conventional process, the present invention provides a process wherein a rhodium catalyst modified with an oxide of an organic trivalent phosphorus compound is separated in a catalytically active state from the reaction mixture and recycled for reuse.

Accordingly, it is an object of the present invention to provide a process for industrially advantageously conducting a hydroformylation reaction of an olefinic compound.

Another object of the present invention is to provide an industrially advantageous process wherein an olefinic compound is hydroformylated in a catalyst solution containing rhodium and an oxide of an organic trivalent phosphorus compound.

A further object of the present invention is to provide a process wherein a rhodium catalyst modified with an oxide of an organic trivalent phosphorus compound is separated in a catalytically active state from the reaction mixture and recycled for the hydroformylation reaction of the olefinic compound.

Namely, the present invention provides a hydroformylation process which comprises hydroformylating an olefinic compound by reacting it with water gas in a catalyst solution containing rhodium and an oxide of an organic trivalent phosphorus compound; adding an organic trivalent phosphorus compound to the reaction mixture, followed by distillation to separate a distillate containing the hydroformylation product from a high-boiling residue containing rhodium; oxidizing the high-boiling residue at the same time as or subsequent to the distillation, to convert the organic trivalent phosphorus compound to its oxide; and recycling the oxidized residue to the hydroformylation reaction zone.

Now, the present invention will be described in detail with reference to the preferred embodiments.

The present invention is concerned with a hydroformylation reaction of an olefinic compound wherein a rhodium catalyst modified with an oxide of an organic trivalent phosphorus compound is separated in a catalytically active state from the reaction mixture and recycled to the hydroformylation reaction zone for reuse.

In the process of the present invention, the first step of the hydroformylation reaction is conducted in accordance with a usual method per se known. The reaction is usually conducted by supplying an olefinic compound and water gas to a catalyst solution which is a solution recycled from a subsequent step and which contains rhodium and an oxide of an organic trivalent phosphorus compound. It is of course possible to additionally supply the catalyst or the solvent, as the case requires. The catalyst may be prepared in the reaction zone by supplying a rhodium compound and an oxide of an organic trivalent phosphorus compound to the hydroformylation reaction zone. However, it is preferred that the rhodium compound and the oxide of an organic trivalent phosphorus compound are preliminarily mixed in a solvent and carbon monoxide is introduced thereto to obtain an active rhodium catalyst, which is then added to the reaction system.

As the rhodium compound to be used for the preparation of the catalyst, there may be mentioned an inorganic acid salt such as rhodium nitrate or rhodium sulfate; an organic acid salt such as rhodium acetate, sodium rhodium oxalate or potassium rhodium malate; and an amine complex salt such as $[RhL_6]X_3$, $[RhL_5, H_2O]X_3$, $[RhL_5(OH)]X_2$, $[RhL_5(NO_2)]X_2$ or $[Rh(Py)_3(NO_3)_2]$ where X is $NO_3^-$, $OH^-$ or $\frac{1}{2}(SO_4^{-2})$, L is $NH_3$ and Py is pyridine. Among them, rhodium nitrate and rhodium acetate are preferably used. Further, a cyclooctadiene complex represented by the general formula $[Rh(RCOO)(COD)]_2$ where R is an alkyl or an aryl group which may be substituted by halogen, and COD is 1,5-cyclooctadiene, may also be used as the above rhodium compound. As the complex represented by the general formula $[Rh(RCOO)(COD)]_2$, there may be mentioned compounds where R is an alkyl group having from 1 to 5 carbon atoms or an aryl group such as a phenyl group which may be substituted by halogen, for instance, $[Rh(CH_3COO)(COD)]_2$, $[Rh(C_2H_5COO)(COD)]_2$, $[Rh(C_6H_5COO)(COD)]_2$, $[Rh(CF_3COO)(COD)]_2$, $[Rh(C_2F_5COO)(COD)]_2$ and $[Rh(CH_2ClCOO)(COD)]_2$. Particularly preferred is a compound where R is a methyl group. When a cyclooctadiene complex is used as the rhodium compound, a catalyst having particularly high catalytic activity and stability is obtainable by preliminarily treating the complex with carbon monoxide or a carbon monoxide-containing gas before it is used as a catalyst for the reaction. For the treatment with carbon monoxide or a carbon monoxide-containing gas, it is usual to employ a method wherein the rhodium compound is dissolved or suspended in the solvent for the hydroformylation reaction, and carbon monoxide or a carbon monoxide-containing gas is blown into the solution or suspension.

The treating conditions are usually selected within such ranges that the carbon monoxide partial pressure is from 1 to 200 kg/cm$^2$, preferably from 1 to 10 kg/cm$^2$, the temperature is from 10° to 200° C., preferably from 20° to 150° C., and the treating time is from 1 to 100 minutes, preferably from 2 to 50 minutes.

The carbon monoxide may be diluted with an inert gas such as nitrogen. Further, water gas may be used. It is extremely advantageous that the treatment can be conducted by means of water gas since water gas is one of the starting materials for the hydroformylation reaction. From the viewpoints of economy and the stability of rhodium, it is preferred that the treatment by means of water gas is conducted at a lower temperature under lower pressure than the corresponding conditions for the hydroformylation reaction which will be described hereinafter. The ratio of hydrogen to carbon monoxide may be the same as the one employed for the hydroformylation reaction which will be described hereinafter, and H$_2$/CO is preferably from $\frac{1}{2}$ to 5/1.

An agitation tank or a foaming tower may be used as the apparatus for the treatment with carbon monoxide or a carbon monoxide-containing gas. More simply, however, a system may be employed wherein a solution containing the rhodium compound is passed through a pipe together with carbon monoxide in a gas-liquid mixed state.

As the oxide of an organic trivalent phosphorus compound, there may be used an arylphosphine oxide such as triphenylphosphine oxide, tritolylphosphine oxide or trianisylphosphine oxide; an alkylphosphine oxide such as tributylphosphine oxide or trioctylphosphine oxide; or an alkylarylphosphine oxide containing both alkyl and aryl groups. Further, there may be used an arylphosphite oxide such as triphenylphosphite oxide or tritolylphosphite oxide; an alkylphosphite oxide such as triethylphosphite oxide, tripropylphosphite oxide or tributylphosphite oxide; or an alkylarylphosphite oxide containing both alkyl and aryl groups. Furthermore, it is possible to use an oxide of a multidentate ligand phosphine such as diphenylphosphinomethane dioxide, diphenylphosphinoethane dioxide, diphenylphosphinobutane dioxide, 1,2-bis(diphenylphosphinomethyl)cyclobutane dioxide or 2,3-O-isopropylidene-2,3-dihydroxy-1,4-bis (diphenylphosphino)butane dioxide.

Such an oxide of an organic trivalent phosphorus compound is preferably used in such an amount that phosphorus in the form of an oxide is present in the hydroformylation reaction zone in a concentration of from 10 to 50 atoms per atom of rhodium. If the amount of the phosphorus in the form of an oxide is too small, the stability of the catalyst tends to decrease. On the other hand, if the phosphorus is excessive, the reaction rate of the hydroformylation tends to decrease.

Further, when an active catalyst is preliminarily prepared from the rhodium compound and the oxide of an organic trivalent phosphorus compound, both materials may be mixed in the above-mentioned ratio and then treated with carbon monoxide. The treating conditions may optionally be selected within such ranges that the carbon monoxide partial pressure is from 1 to 200 kg/cm$^2$, preferably from 1 to 10 kg/cm$^2$, the temperature is from 10° to 200° C., preferably from 20° to 150° C. and the treating time is from 1 to 100 minutes, preferably from 2 to 50 minutes. In this case, it is preferred to use carbon monoxide which does not substantially contain hydrogen.

The catalyst concentration in the reaction zone is usually from 1 to 500 mg/l, preferably from 2 to 100 mg/l, as rhodium.

As the olefinic compound to be used for the hydroformylation reaction, there may be mentioned, in addition to a straight chain α-olefin such as ethylene, propylene, butene-1, pentene-1, hexene-1, octene-1 or decene-1, a straight chain internal olefin such as butene-2, pentene-2, hexene-2, hexene-3, octene-2 or octene-3, a branched α-olefin such as isobutylene, 2-methylbutene-1, 2-methylpentene-1, 3-methylpentene-1, 2-methylhexene-1, 3-methylhexene-1, 2-methylheptene-1, 3-methylheptene-1 or 4-methylheptene-1, a multi branched α-olefin such as 2,3-dimethylbutene-1, 2,3-dimethylpentene-1, 2,4-dimethylpentene-1, 2,3-dimethylhexene-1, 2,4-dimethylhexene-1, 2,5-dimethylhexene-1, or 3,4-dimethylhexene-1, and double bond isomers thereof.

Further, there may also be used a mixture of isomers such as dimers to tetramers of e.g. propylene, butene or isobutylene, or an olefin having a substituent such as allyl alcohol, acrolein acetal, vinyl acetate, styrene or an alkylvinyl ether. The present invention is particularly advantageous when applied to the hydroformylation of a mixture of isomers such as dimers to tetramers of e.g. propylene, butene or isobutylene. These materials are branched internal olefins or mixtures mainly composed of branched internal olefins, which are hardly hydroformylated with the rhodium catalyst modified with an organic phosphine. As opposed to the case where the rhodium catalyst modified with an organic phosphine is used, the reaction can readily be conducted according to the present invention even when these mixtures of isomers are used as the starting materials.

In the present invention, a solution containing rhodium and an oxide of an organic trivalent phosphorus compound, which is recycled from a subsequent step, is used as the reaction medium, as mentioned above. However, an additional solvent may also be used. As the solvent, any optional solvent may be used so long as it is capable of dissolving the catalyst and does not adversely affect the reaction. For instance, there may be used an aromatic hydrocarbon such as benzene, toluene, xylene or dodecylbenzene, an alicyclic hydrocarbon such as cyclohexane; an ether such as dibutyl ether, ethylene glycol dimethyl ether, diethylene glycol diethyl ether, triethylene glycol dimethyl ether or tetrahydrofuran; or an ester such as diethylphthalate or dioctylphthalate. Further, an aldehyde or alcohol formed by the hydroformylation reaction may also be used as the solvent.

From the viewpoint of the reaction rate, it is advantageous that the reaction temperature is higher. However, if the reaction temperature is too high, it is likely that the catalyst will decompose. Accordingly, it is usually preferred to conduct the reaction at a temperature of from 50° to 170° C., particularly from 100° to 150° C.

As the water gas, it is preferred that the molar ratio of hydrogen to carbon monoxide is from 1/5 to 5/1, particularly from $\frac{1}{2}$ to 2/1. The partial pressure of the water gas is preferably from 20 to 500 kg/cm$^2$, particularly from 50 to 300 kg/cm$^2$.

The reaction can be conducted in a continuous system or in a batch system.

To the reaction mixture obtained by the hydroformylation reaction, an organic trivalent phosphorus compound is added, and then the mixture is subjected to distillation to distill an aldehyde or alcohol formed by the reaction.

As the organic trivalent phosphorus compound, there may be used an arylphosphine such as triphenylphosphine, tritolylphosphine or trianisylphosphine; an alkylphosphine such as tributylphosphine or trioctylphosphine; or an alkylarylphosphine having both alkyl and aryl groups. Further, an arylphosphite such as triphenylphosphite or tritolylphosphite; an alkylphosphite such as triethylphosphite, tripropylphosphite or tributylphosphite; or an alkylarylphosphite having both alkyl and aryl groups may also be used. Furthermore, it is possible to use a multidentate ligand phosphine such as diphenylphosphinomethane, diphenylphosphinoethane, diphenylphosphinobutane, 1,2-bis(diphenylphosphinomethyl) cyclobutane or 2,3-O-iso-propylidene-2,3-dihydroxy-1,4-bis(diphenylphosphino)butane.

As the organic trivalent compound, it is preferred to use the one which corresponds to the oxide of an organic trivalent phosphorus compound present in the catalyst solution for the hydroformylation reaction. Usually, triphenylphosphine or tributylphosphine is used. The organic trivalent phosphorus compound will establish a coordination with the rhodium catalyst in the reaction mixture and thus serves to stabilize the rhodium catalyst. The organic trivalent phosphorus compound is added in such an amount that the phosphorus in a trivalent state is at least one atom per atom of rhodium. However, even when the organic trivalent phosphorus compound is used in a great amount, the stability of the catalyst does not necessarily increase in proportion to the added amount. Therefore, the phosphorus compound is added usually in such an amount that the phosphorus in the trivalent state is from 1 to 100 atoms, preferably from 1 to 20 atoms, per atom of rhodium.

The hydroformylation reaction mixture thus added with the organic trivalent phosphorus compound is subjected to distillation in a usual manner to separate a distillate having a low boiling point such as an aldehyde or alcohol from the residue having a high boiling point containing rhodium. The rhodium catalyst in the reaction mixture is stabilized by the organic trivalent phosphorus compound, and accordingly an optional distillation system such as a flush distillation, a normal pressure distillation, a reduced pressure distillation or a combination thereof may be employed. The distillation temperature is preferably not higher than 200° C., particularly from 25° to 150° C.

In the process of the present invention, the high-boiling residue is oxidized at the same time as or subsequent to the distillation operation to convert the organic trivalent phosphorus compound to its oxide.

In order to oxidize the high-boiling residue at the same time as the distillation operation to convert the organic trivalent phosphorus compound to its oxide, the distillation may be conducted in the presence of molecular oxygen, for example, in the distillation tower. Usually, the distillation is conducted while supplying a small amount of air into the distillation tower, whereby the distillation and the oxidation of the organic trivalent compound can be done at the same time. For instance, in the case of a reduced pressure distillation tower, a certain amount of air usually comes in, and the oxidation of the organic trivalent phosphorus compound proceeds even with such a small amount of the incoming air. If the oxidation in the tower does not proceed adequately, the high-boiling residue discharged from the bottom of the tower may be subjected again to an oxidation in the following manner.

In order to oxidize the high-boiling residue subsequent to the distillation operation to convert the organic trivalent phosphorus compound to its oxide, the oxidation treatment may be conducted in the presence of molecular oxygen or a peroxide in accordnace with a usual method. In the case of oxidizing the high-boiling residue in the presence of molecular oxygen, the oxidation may usually be conducted by blowing air into the high-boiling residue under atmospheric pressure. The oxidation conditions are optionally selected within such ranges that the temperature is from room temperature to 200° C., preferably from room temperature to 150° C., and the oxidation time is from 1 minute to 5 hours, preferably from 5 minutes to 2 hours.

In the case of oxidizing the high-boiling residue in the presence of a peroxide, said residue is recycled to the hydroformylation reaction zone together with said peroxide. As the peroxide to be used for this purpose, there may be mentioned an organic peroxide such as benzoyl peroxide, t-butyl peroxide or lauroyl peroxide; and an inorganic peroxide such as hydrogen peroxide. It is preferred to use an organic peroxide obtained by the air oxidation of an olefin, particularly an olefinic compound which is used as a raw material for the hydroformylation. Namely, when air is blown into the raw material olefinic compound, a part of the olefinic compound is converted to a peroxide, and it is preferred to feed the air-treated olefinic compound containing the peroxide to the hydroformylation reaction zone together with the high-boiling residue containing rhodium.

The above-mentioned oxidation treatment is intended to convert the organic trivalent phosphorus compound contained in the high-boiling residue to the corresponding oxide. However, it is unnecessary to convert all of the organic trivalent phosphorus compound to the corresponding oxide. According to the research conducted by the present inventors, it has been found that while the organic trivalent phosphorus compound in a free state is readily oxidized to the corresponding oxide, the organic phosphorus compound coordinated with rhodium is hardly oxidized. Particularly, among the organic phosphorus compounds coordinated with rhodium, the last one is extremely hardly oxidized. It is considered that since this remains to be coordinated with rhodium without being oxidized, the catalyst remains to be stable without undergoing decomposition even in the absence of carbon monoxide. Further, it is considered that when the oxidation-treated high-boiling residue is recycled to the hydroformylation reaction zone, this unoxidized organic phosphorus compound gradually reaches the dissociation equilibrium, whereby it is freed from rhodium and then oxidized to its oxide by oxygen which is present in a very small amount as an impurity.

The oxidation-treated high-boiling residue is recycled to the reaction zone for the hydroformylation reaction and reused as the catalyst solution or its part. Further, in this residue, high-boiling byproducts and phosphorus compounds produced by side reactions tend to accumulate, and accordingly it is preferred to continuously or intermittently discharge a part of them out of the reaction zone to maintain their concentration in the reaction zone to be constant.

According to the present invention, the rhodium catalyst can be recycled in an active state as dissolved in the solution.

Now, the present invention will be described in further detail with reference to an example. However, it should be understood that the present invention is by no means restricted by such a specific example.

EXAMPLE 1

Into a top and bottom agitation type SUS-316 autoclave having an internal capacity of 500 ml, 250 ml of butene dimers (i.e. a mixture of double bond isomers comprising n-octene, 3-methylheptene and 3,4-dimethylhexene), 15.8 g of a methanol solution of rhodium acetate (i.e. 1.3 mg/g as rhodium metal) and 558 mg (i.e. 10 times in molar ratio to the rhodium) of triphenylphosphine oxide were fed. The autoclave was flushed with nitrogen gas, and the nitrogen gas was pressurized upto 20 kg/cm$^2$G and then released to atmospheric pressure. This operation was repeated 3 times, and then the temperature was raised to 130° C. Immediately after the temperature reached 130° C., water gas (H$_2$/CO=1) was introduced under pressure to bring the total pressure to a level of 200 kg/cm$^2$G, and the reaction was conducted at 130° C. for 4 hours. During this period, water gas was supplemented from an accumulator via a constant pressure control apparatus to compensate the water gas consumed by the reaction, whereby the autoclave was maintained under pressure of 200 kg/cm$^2$G. After the completion of the reaction, the reaction mixture was analyzed by gas chromatography, whereby the yield of C$_9$-aldehyde was found to be 92% and the yield of C$_9$-alcohol was found to be 6%.

To 100 ml of this reaction mixture, 88 mg (i.e. 5 times in molar ratio to the rhodium) of triphenylphosphine was added, and while permitting air to enter, the mixture was distilled under reduced pressure of 10 mmHg at 130° C., whereupon 87 ml of a distillate was obtained. The distillation residue was subjected to oxidation treatment by maintaining it in an air atmosphere under atmospheric pressure at 140° C. for 2 hours.

Into a top and bottom agitation type SUS-316 autoclave having an internal capacity of 200 ml, 50 ml of butene dimers were introduced and the above-mentioned oxidation-treated distillation residue was added to bring the rhodium concentration to 10 mg/l. Nitrogen gas was introduced into the autoclave to bring the pressure to 20 kg/cm$^2$G and then released to atmospheric pressure. This operation was repeated 3 times, and then the temperature was raised to 130° C. Immediately after the temperature reached 130° C., water gas was introduced under pressure to bring the total pressure to 200 kg/cm$^2$G, and the reaction was conducted at 130° C. for 4 hours. During this period, water gas was supplemented from an accumulator via a constant pressure control apparatus to compensate the water gas consumed by the reaction, whereby the autoclave was maintained under pressure of 200 kg/cm$^2$G. After the completion of the reaction, the reaction mixture was analyzed by gas chromatography, whereby the yield of C$_9$-aldehyde was found to be 89% and the yield of C$_9$-alcohol was found to be 2%.

COMPARATIVE EXAMPLE 1

To 100 ml of the reaction mixture obtained by the former half of the process of Example 1, 88 mg (i.e. 5 times in molar ratio to the rhodium) of triphenylphosphine was added, and the mixture was distilled under reduced pressure of 10 mmHg in a nitrogen gas atmosphere at 130° C., whereupon 87 ml of a distillate was obtained. The distillation residue was used for the hydroformylation reaction under the same conditions as in the latter half of the process of Example 1, whereby the yield of C$_9$-aldehyde was 42% and the yield of C$_9$-alcohol was 9%.

We claim:

1. A hydroformylation process which comprises hydroformylating an olefinic compound selected from the group consisting of dimers, trimers and tetramers of propylene, butene or isobutylene, by reacting said olefinic compound with water gas at a temperature of from 50° to 170° C. under water gas partial pressure of from 20 to 500 kg/cm$^2$ in a catalyst solution containing rhodium, an oxide of an organic trivalent phosphorus compound present in an amount such that the phosphrous concentration is at least 10 atoms per atom of rhodium, and high boiling by-products produced by side reactions, to form a hydroformylation product composed mainly of an aldehyde having a carbon atom number greater by one than the starting olefinic compound; adding an organic trivalent phosphrous compound to the reaction mixture, followed by distillation to separate a distillate containing the hydroformylation product from a high-boiling residue containing rhodium; oxidizing the high-boiling residue at the same time or as subsequent to the distillation, to convert the organic trivalent phosphorus compound to its oxide; and recycling the oxidized residue to the hydroformylation reaction zone.

2. The process according to claim 1, wherein the distillation is conducted in the presence of molecular oxygen to oxidize the high-boiling residue and to convert the organic trivalent phosphorus compound to its oxide.

3. The process according to claim 1, wherein the high-boiling residue obtained by the distillation is oxidized in the presence of molecular oxygen to convert the organic trivalent phosphorus compound to its oxide.

4. The process according to claim 1, wherein to the reaction mixture obtained by the hydroformylation reaction, the organic trivalent phosphorus compound is added to bring the concentration of trivalent phosphorus atoms to be from 1 to 20 atoms per atom of the rhodium in the mixture.

5. The process according to claim 2, wherein the organic trivalent phosphorus compound is added to the reaction mixture obtained by the hydroformylation reaction in a quantity sufficient to bring the concentration of trivalent phosphorus atoms to from 1 to 20 atoms per atom of the rhodium in the mixture.

6. The process according to claim 3, wherein the organic trivalent phosphorus compound is added to the reaction mixture obtained by the hydroformylation reaction in a quantity sufficient to bring the concentration of trivalent phosphorus atoms to from 1 to 20 atoms per atom of the rhodium in the mixture.

7. The process of claim 1, wherein the oxide of the organic trivalent phosphorus compound is present in the catalyst solution in an amount such that the phosphorus concentration in the hydroformylation reaction zone is from 10 to 50 atoms per atom of rhodium.

8. The process of claim 1, wherein said catalyst solution further comprises a solvent.

9. The hydroformylation process of claim 1, wherein the oxide of an organic trivalent phosphorus compound comprises an arylphosphine oxide, an alkylphosphine oxide, an alkylarylphosphine oxide, an arylphosphite oxide, an alkylphosphite oxide, an alkylarylphosphite oxide, a multidentate phosphine oxide or a mixture thereof.

10. The hydroformylation process of claim 1, wherein the oxide of an organic trivalent phosphorus compound comprises triphenylphosphine oxide, tritolylphosphine oxide, trianisylphosphine oxide, tributylphosphine oxide, trioctylphosphine oxide, triphenylphosphite oxide, tritolylphosphite oxide, triethylphosphite oxide, tripropylphosphite oxide, tributylphosphite oxide, diphenylphosphinomethane dioxide, diphenylphosphinoethane dioxide, diphenylphosphinobutane dioxide, 1,2-bis(diphenylphosphinomethyl)cyclobutane dioxide, 2,3-O-isopropylidene-2,3-dihydroxy-1,4-bis-(diphenylphosphino)butane dioxide or mixtures thereof.

11. The hydroformylation process of claim 1, wherein the rhodium concentration in the reaction zone is from 1 to 500 mg/l.

12. The process of claim 8, wherein said solvent comprises an aromatic hydrocarbon, an alicyclic hydrocarbon, an ether, an ester, an aldehyde, an alcohol or a mixture thereof.

13. The process of claim 8, wherein said solvent comprises benzene, toluene, xylene, dodecylbenzene, cyclohexane, dibutyl ether, ethylene glycol dimethyl ether, diethylene glycol diethyl ether, triethylene glycol dimethyl ether, tetrahydrofuran, diethylphthalate, dioctylphthalate or a mixture thereof.

14. The hydroformylation process of claim 1, wherein the water gas comprises hydrogen to carbon monoxide in a ratio of from 1/5 to 5/1.

15. The hydroformylation process of claim 1, wherein said reaction is conducted in a continuous system or in a batch system.

* * * * *